(12) United States Patent
Jacobs et al.

(10) Patent No.: US 12,567,146 B2
(45) Date of Patent: Mar. 3, 2026

(54) SYSTEMS AND METHODS FOR DETECTING AND CHARACTERIZING COVID-19

(71) Applicant: THE JOHNS HOPKINS UNIVERSITY, Baltimore, MD (US)

(72) Inventors: Michael A. Jacobs, Sparks, MD (US); Vishwa Sanjay Parekh, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 268 days.

(21) Appl. No.: 18/554,656

(22) PCT Filed: Apr. 14, 2022

(86) PCT No.: PCT/US2022/024883
§ 371 (c)(1),
(2) Date: Oct. 10, 2023

(87) PCT Pub. No.: WO2022/225794
PCT Pub. Date: Oct. 27, 2022

(65) Prior Publication Data
US 2024/0370997 A1 Nov. 7, 2024

Related U.S. Application Data

(60) Provisional application No. 63/178,705, filed on Apr. 23, 2021.

(51) Int. Cl.
| | |
|---|---|
| *G06T 7/00* | (2017.01) |
| *G06N 3/0464* | (2023.01) |
| *G16H 10/60* | (2018.01) |

(52) U.S. Cl.
CPC ......... *G06T 7/0012* (2013.01); *G06N 3/0464* (2023.01); *G16H 10/60* (2018.01);
(Continued)

(58) Field of Classification Search
CPC ......... G06T 7/0012; G06T 2207/10081; G06T 2207/20084; G06T 2207/30008;
(Continued)

(56) References Cited

U.S. PATENT DOCUMENTS

| | | | | |
|---|---|---|---|---|
| 11,076,824 B1 * | 8/2021 | Wang | ..................... | G06N 3/044 |
| 11,694,319 B2 * | 7/2023 | Kang | ..................... | G06N 20/20 |
| | | | | 382/100 |

(Continued)

FOREIGN PATENT DOCUMENTS

| | | |
|---|---|---|
| AU | 2021100007 A4 | 3/2021 |
| CN | 111415356 A | 7/2020 |

OTHER PUBLICATIONS

Doherty, F. (Authorized officer), International Preliminary Report on Patentability in corresponding International Application No. PCT/US2022/024883 mailed on Nov. 2, 2023, 6 pages.
(Continued)

*Primary Examiner* — Tom Y Lu
(74) *Attorney, Agent, or Firm* — MH2 Technology Law Group LLP

(57) ABSTRACT

A method includes receiving one or more radiological images of an anatomy of a patient. The method also includes identifying a boundary of different tissue types in the anatomy of the patient based at least partially upon the one or more radiological images. The method also includes identifying one or more regions within the boundary. The one or more regions include a lung region. The method also includes identifying healthy tissue and COVID-19 tissue in the lung region. The method also includes quantifying an extent of the COVID-19 tissue in the lung region by comparing an amount of the COVID-19 tissue in the lung region to an amount of the healthy tissue in the lung region. The method also includes classifying the extent of the COVID-
(Continued)

19 tissue in the lung region into one or more of a plurality of COVID-19 classes.

19 Claims, 16 Drawing Sheets

(52) U.S. Cl.
CPC ............... *G06T 2207/10081* (2013.01); *G06T 2207/20084* (2013.01); *G06T 2207/30008* (2013.01); *G06T 2207/30048* (2013.01); *G06T 2207/30061* (2013.01)

(58) Field of Classification Search
CPC G06T 2207/30048; G06T 2207/30061; G06N 3/0464; G16H 10/60
See application file for complete search history.

(56) References Cited

U.S. PATENT DOCUMENTS

| | | | | |
|---|---|---|---|---|
| 12,026,877 | B2 * | 7/2024 | Li | ........................... G06V 10/82 |
| 2013/0151441 | A1 | 6/2013 | Archambeau et al. | |
| 2022/0036564 | A1 * | 2/2022 | Ye | ............................. G06T 7/11 |
| 2022/0284586 | A1 * | 9/2022 | El-Baz | .................. G06T 7/0012 |
| 2023/0100740 | A1 * | 3/2023 | Malur Srinivasan | ........................ G06F 18/2431 382/157 |
| 2023/0230705 | A1 * | 7/2023 | El-Baz | .................. G06T 7/0012 702/19 |

OTHER PUBLICATIONS

Wang et al., "Multiscale rotation-invariant convolutional neural networks for lung texture classification." IEEE journal of biomedical and health informatics 22.1 (2017): 184-195.

Rodriquez, K. (Authorized officer), International Search Report and Written Opinion in corresponding International Application No. PCT/US2022/024883 mailed on Sep. 1, 2022, 7 pages.

* cited by examiner

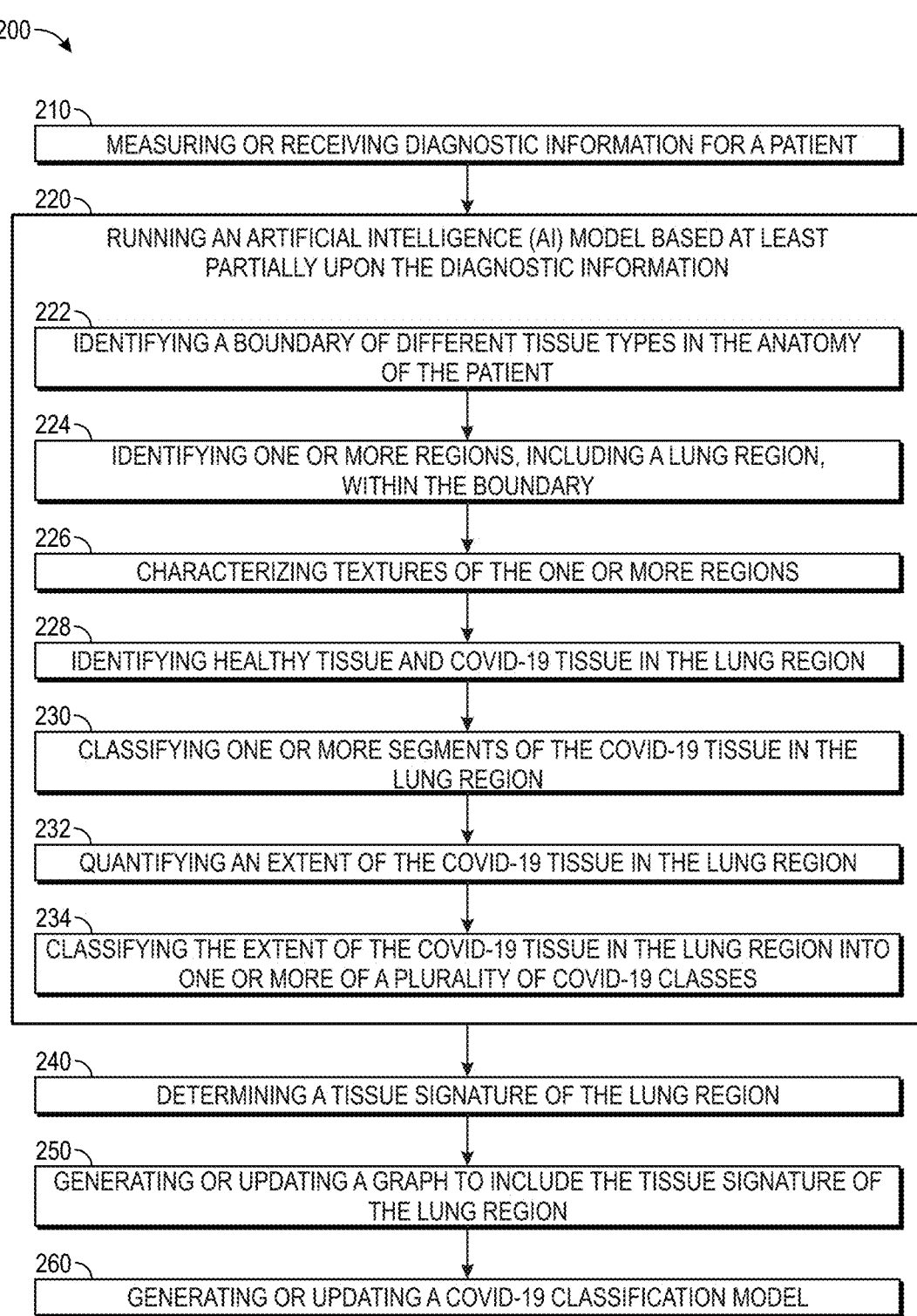

200

210 — MEASURING OR RECEIVING DIAGNOSTIC INFORMATION FOR A PATIENT

220 — RUNNING AN ARTIFICIAL INTELLIGENCE (AI) MODEL BASED AT LEAST PARTIALLY UPON THE DIAGNOSTIC INFORMATION

222 — IDENTIFYING A BOUNDARY OF DIFFERENT TISSUE TYPES IN THE ANATOMY OF THE PATIENT

224 — IDENTIFYING ONE OR MORE REGIONS, INCLUDING A LUNG REGION, WITHIN THE BOUNDARY

226 — CHARACTERIZING TEXTURES OF THE ONE OR MORE REGIONS

228 — IDENTIFYING HEALTHY TISSUE AND COVID-19 TISSUE IN THE LUNG REGION

230 — CLASSIFYING ONE OR MORE SEGMENTS OF THE COVID-19 TISSUE IN THE LUNG REGION

232 — QUANTIFYING AN EXTENT OF THE COVID-19 TISSUE IN THE LUNG REGION

234 — CLASSIFYING THE EXTENT OF THE COVID-19 TISSUE IN THE LUNG REGION INTO ONE OR MORE OF A PLURALITY OF COVID-19 CLASSES

240 — DETERMINING A TISSUE SIGNATURE OF THE LUNG REGION

250 — GENERATING OR UPDATING A GRAPH TO INCLUDE THE TISSUE SIGNATURE OF THE LUNG REGION

260 — GENERATING OR UPDATING A COVID-19 CLASSIFICATION MODEL

FAT

NORMAL
LUNG

MUSCLE

BONE

CV-19

COMPUTED TOMOGRAPHY
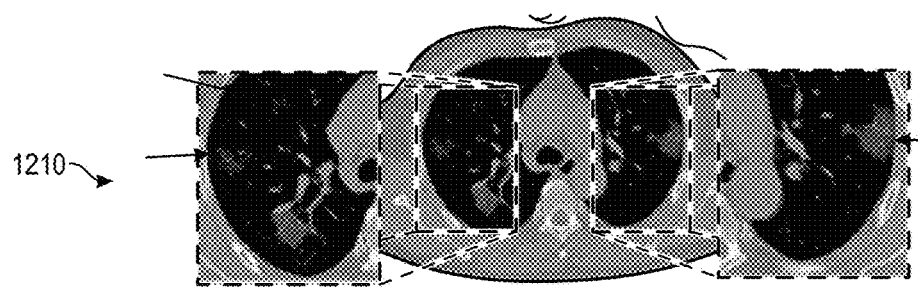
1210
COVID DEEP LEARNING
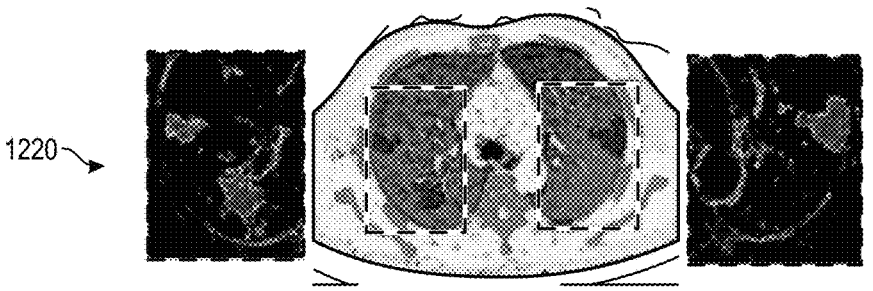
1220
COVID DEEP LEARNING SEGMENTATION
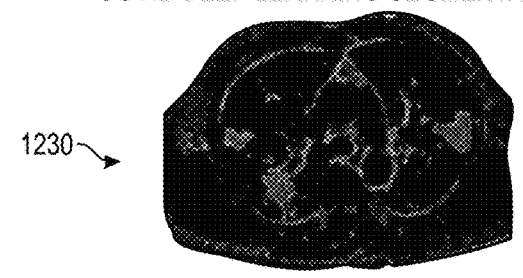
1230
COVID RADIOMICS ENTROPY
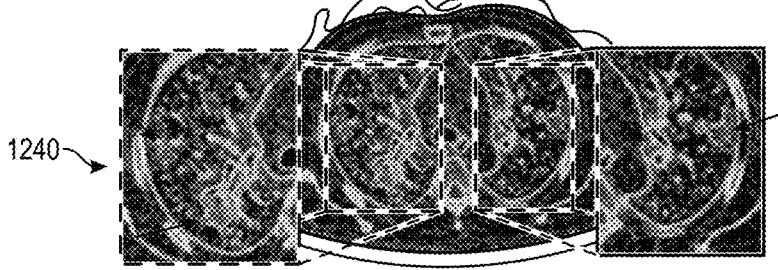
1240
COVID RADIOMICS CLONALITY
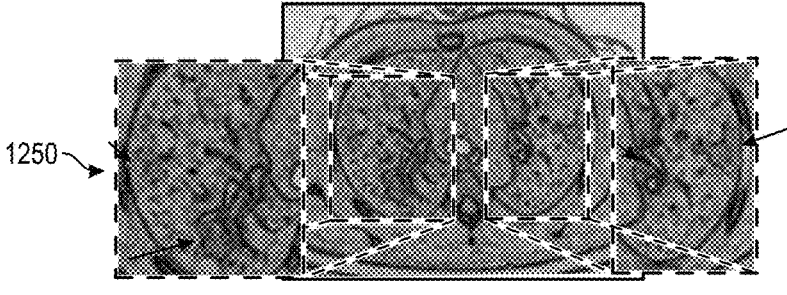
1250
FIG. 12

SYSTEMS AND METHODS FOR DETECTING AND CHARACTERIZING COVID-19

CROSS-REFERENCE TO RELATED APPLICATIONS

This application is the national stage entry of International Patent Application No. PCT/US2022/024883, filed on Apr. 14, 2022, and published as WO 2022/225794 A1 on Oct. 27, 2022, which claims the benefit of U.S. Provisional Patent Application Ser. No. 63/178,705, filed Apr. 23, 2021, both of which are hereby incorporated by reference herein in their entireties.

FIELD OF THE INVENTION

The present invention relates generally to systems and methods for detecting and characterizing COVID-19 (CV-19). More particularly, the present invention relates to systems and methods for generating and using a radiological decision support framework to detect and characterize CV-19 in lungs of a patient.

BACKGROUND OF THE INVENTION

Early detection and characterization of COVID-19 (CV-19) may facilitate treatment for patients. One current diagnostic method uses chest X-rays (CXR) and computed tomography (CT) scans to provide visual and subjective information of the disease. However, existing computer aided design (CAD) systems do not capture or use quantitative metrics. Moreover, existing CAD systems do not use radiomics, machine learning, or deep learning methods for combining and providing visualization and characterization of CV-19 data. In addition, existing CAD systems use only small portions of the data for diagnosis and not all available data. Existing CAD systems also do not classify any abnormal findings and only show a rough approximation of the relevant locations. This limits the ability for a physician to be confident in diagnosing and determining the extent of CV-19 in a patient.

SUMMARY OF THE INVENTION

A computing system for detecting and characterizing COVID-19 tissue in a lung region of a patient is disclosed. The computing system includes one or more processors and a memory system. The memory system includes one or more non-transitory computer-readable media storing instructions that, when executed by at least one of the one or more processors, cause the computing system to perform operations. The operations include receiving one or more radiological images of an anatomy of a patient, pathology results for the patient, symptomology for the patient, and a medical history of the patient. The operations also include running an artificial intelligence model based at least partially upon the radiological images, the pathology results, the symptomology, and the medical history. Running the artificial intelligence model includes identifying a boundary of different tissue types in the anatomy of the patient using a semantic segmentation model. Running the artificial intelligence model also includes identifying one or more regions within the boundary using a multiscale texture signature convolutional neural network (MTS-CNN) model. The one or more regions include a lung region, a heart region, a liver region, a bone region, a muscle region, and a fat region. Running the artificial intelligence model also includes characterizing textures of the one or more regions using radiomics. Running the artificial intelligence model also includes identifying healthy tissue and COVID-19 tissue in the lung region. Running the artificial intelligence model also includes classifying one or more segments of the COVID-19 tissue in the lung region as ground glass opacity, crazy paving pattern, consolidation, or a combination thereof based at least partially upon the one or more radiological images and the textures. The one or more segments are classified using a multitask regression and classification (MTRC) model. Running the artificial intelligence model also includes quantifying an extent of the COVID-19 tissue in the lung region as a ratio by comparing an amount of the COVID-19 tissue in the lung region to an amount of the healthy tissue in the lung region. Running the artificial intelligence model also includes classifying the extent of the COVID-19 tissue in the lung region into one or more of a plurality of COVID-19 classes defined by radiological nomenclature. The operations also include determining a tissue signature of the lung region based at least partially upon the classification of the extent of the COVID-19 tissue in the lung region. The operations also include generating or updating a scattergram to include the tissue signature of the lung region. The operations also include generating or updating a COVID-19 classification model based at least partially upon the one or more radiological images, the pathology results, the symptomology, the medical history, and the scattergram.

A method for detecting and characterizing COVID-19 tissue is also disclosed. The method includes receiving one or more radiological images of an anatomy of a patient. The method also includes running an artificial intelligence model based at least partially upon the radiological images. Running the artificial intelligence model includes identifying a boundary of different tissue types in the anatomy of the patient using a semantic segmentation model. Running the artificial intelligence model also includes identifying one or more regions within the boundary using a multiscale texture signature convolutional neural network (MTS-CNN) model. The one or more regions include a lung region. Running the artificial intelligence model also includes identifying healthy tissue and COVID-19 tissue in the lung region. Running the artificial intelligence model also includes classifying one or more segments of the COVID-19 tissue in the lung region based at least partially upon the one or more radiological images. The one or more segments are classified using a multitask regression and classification (MTRC) model. Running the artificial intelligence model also includes quantifying an extent of the COVID-19 tissue in the lung region as a ratio by comparing an amount of the COVID-19 tissue in the lung region to an amount of the healthy tissue in the lung region. Running the artificial intelligence model also includes classifying the extent of the COVID-19 tissue in the lung region into one or more of a plurality of COVID-19 classes. The method also includes determining a tissue signature of the lung region based at least partially upon the classification of the extent of the COVID-19 tissue in the lung region. The method also includes generating or updating a scattergram to include the tissue signature of the lung region.

In another embodiment, the method includes receiving one or more radiological images of an anatomy of a patient. The method also includes identifying a boundary of different tissue types in the anatomy of the patient based at least partially upon the one or more radiological images. The method also includes identifying one or more regions within the boundary. The one or more regions include a lung region. The method also includes identifying healthy tissue and COVID-19 tissue in the lung region. The method also includes quantifying an extent of the COVID-19 tissue in the lung region by comparing an amount of the COVID-19 tissue in the lung region to an amount of the healthy tissue in the lung region. The method also includes classifying the extent of the COVID-19 tissue in the lung region into one or more of a plurality of COVID-19 classes.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 2 illustrates a flowchart of a method for detecting and classifying CV-19 in a lung region of a patient, according to an embodiment.

FIG. 12 illustrates a demonstration of the IC-RADS output using the CT images, according to an embodiment.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present disclosure is directed to a system and method for detecting and characterizing COVID-19 (CV-19). More particularly, the present disclosure is directed to an intelligent CV-19 radiological assessment and diagnostics system (IC-RADS). IC-RADS may provide interpretation and/or triaging of patients with CV-19. IC-RADS may also or instead be used for the initial presentation of the patient, monitoring during a hospital stay, and/or post-treatment of the patient, to gauge the response of the patient.

IC-RADS may use diagnostic tools for the early detection, characterization, and/or classification of CV-19 in different lung tissue types with high specificity and sensitivity. IC-RADS may also or instead use diagnostics and radiomics with machine learning (ML) and/or deep learning information. More particularly, IC-RADS may detect, segment, and classify the diagnostics using radiological images using one or more CV-19 tissue signature vectors from different information sources (e.g., tissue, blood, physical exam, etc.) and one or more images by creating a ML embedded image for potential targets and extent of disease. IC-RADS can be used in combination with blood antibodies, smears, or the like.

Figure 1:
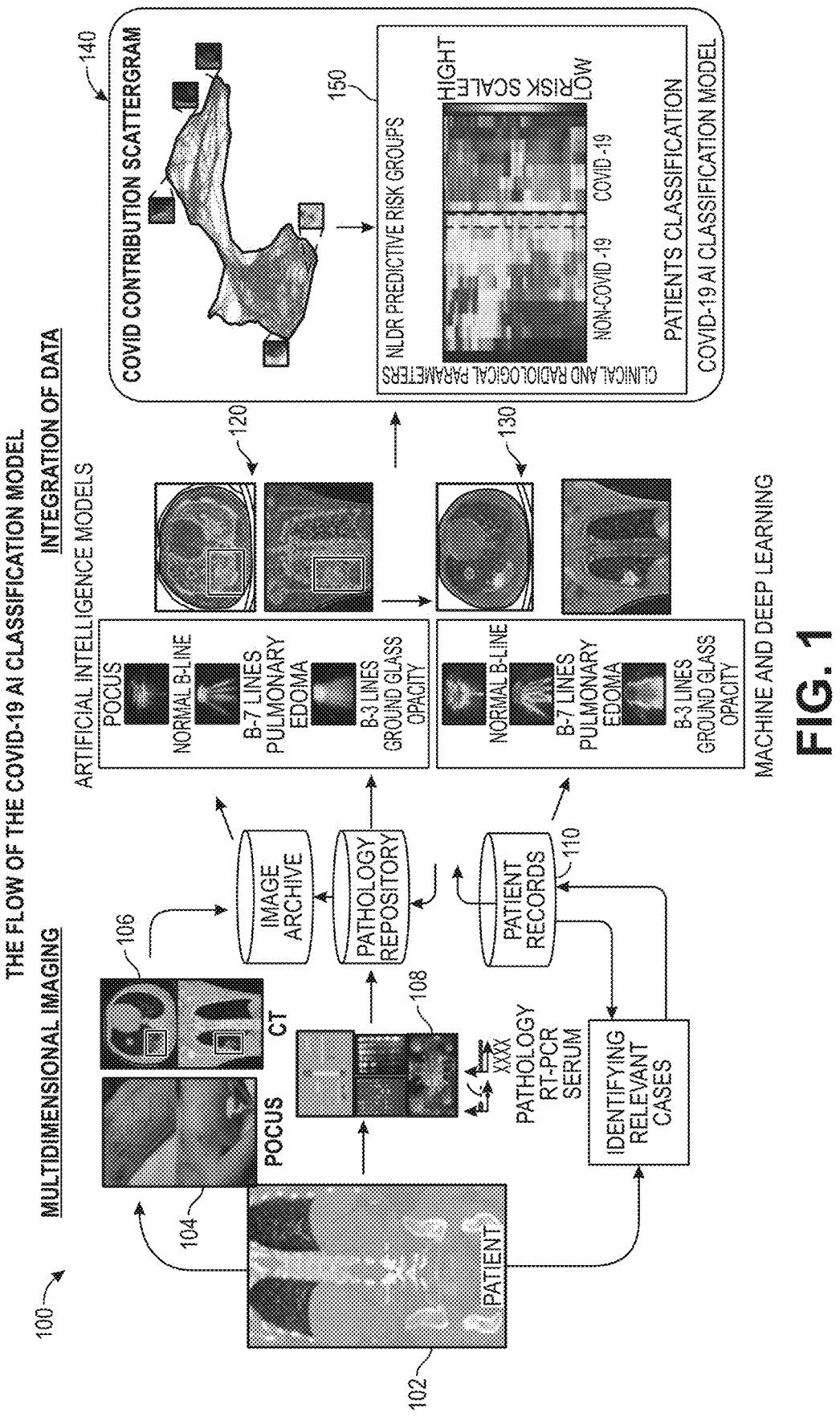
FIG. 1 illustrates a schematic view of a flow of a CV-19 artificial intelligence (AI) classification model, according to an embodiment.

FIG. 1 illustrates a schematic view of a flow of a CV-19 artificial intelligence (AI) classification model 100, according to an embodiment. The model 100 may receive diagnostic information such as X-ray images 102, ultrasound (e.g., point of care ultrasound) images 104, computed tomography (CT) images (also referred to as CT scans) 106, or a combination thereof. The diagnostic information may also include pathology results 108 such as blood samples, reverse transcription polymerase chain reaction (RT-PCR) samples, or a combination thereof. The diagnostic information may also include a medical history for the patient (e.g., the patient's medical records) 110.

An artificial intelligence (AI) model may then generate one or more images 220 based at least partially upon the diagnostic information. A ML and/or deep learning model may then generate one or more images 230 based at least partially upon the diagnostic information and/or the images 220 from the AI model. The diagnostic information, the images 220, the images 230, or a combination thereof may be used to generate or update a CV-19 contribution scattergram 240. The diagnostic information, the images 220, the images 230, the scattergram 240, or a combination thereof may be used to generate or update a COVID-19 classification model 250. Additional details about the CV-19 AI classification model 100 are provided below.

FIG. 2 illustrates a flowchart of a method 200 for detecting and classifying CV-19 in a lung region of a patient, according to an embodiment. An illustrative order of the method 200 is provided below; however, one or more steps of the method 200 may be performed in a different order, performed simultaneously, repeated, or omitted.

The method 200 may include measuring or receiving diagnostic information for a patient, as at 210. The diagnostic information may be or include one or more radiological images (e.g., images 102, 104, 106) of an anatomy of a patient, pathology results 108 for the patient, symptomology for the patient, a medical history 110 of the patient, or a combination thereof.

The method 200 may also include running an artificial intelligence (AI) model based at least partially upon the diagnostic information, as at 220.

Running the AI model may include identifying a boundary of different tissue types in the anatomy of the patient, as at 222. For example, this may include identifying a boundary of (or between) lung tissue and other tissue outside the lung, for example, fatty tissue, ribs, muscle, and other organs. Within the lungs, both lungs (e.g., right and left) may be segmented, and a boundary may be created between the heart and pulmonary vessels. The boundary may be identified using a first type of model (e.g., a semantic segmentation model).

Running the AI model may also include identifying one or more regions within the boundary, as at 224. For example, the one or more regions may include a lung region, a heart region, a liver region, a bone region, a muscle region, a fat region, or a combination thereof. The one or more regions may be identified using second type of model (e.g., a multiscale texture signature convolutional neural network (MTS-CNN) model).

Running the AI model may also include characterizing one or more textures of the one or more regions, as at 226. For example, the texture(s) may be or include gray-scale patterns, inter-pixel relationships, or shape-based properties of the one or more regions. The textures may be characterized using radiomics.

Running the AI model may also include identifying healthy tissue and COVID-19 tissue in the lung region, as at 228. As used herein, "healthy tissue" refers to tissue that is not infected with COVID-19, and "COVID-19 tissue" refers to tissue that is infected with COVID-19.

Running the AI model may also include classifying one or more segments of the COVID-19 tissue in the lung region, as at 230. The one or more segments may be classified as ground glass opacity, crazy paving pattern, consolidation, or a combination thereof. The one or more segments may be classified based at least partially upon the one or more radiological images, the textures, of a combination thereof. The one or more segments may be classified using a third type of model (e.g., a multitask regression and classification (MTRC) model).

Running the AI model may also include quantifying an extent of the COVID-19 tissue in the lung region, as at 232. In one embodiment, the extent of the COVID-19 tissue in the lung region may be quantified as a ratio by comparing an amount of the COVID-19 tissue in the lung region to an amount of the healthy tissue in the lung region. In another embodiment, the extent of the COVID-19 tissue in the lung region may be quantified as a ratio by comparing an amount of the COVID-19 tissue in the lung region to the total amount of tissue in the lung region.

Running the AI model may also include classifying the extent of the COVID-19 tissue in the lung region into one or more of a plurality of COVID-19 classes, as at 234. The COVID-19 classes may be defined by radiological nomenclature. For example, the COVID-19 classes may include typical, indeterminate, and/or atypical.

The method 200 may also include determining a tissue signature of the lung region, as at 240. The tissue signature may be determined based at least partially upon the classification of the extent of the COVID-19 tissue in the lung region. As used herein, the term "tissue signature" refers to the unique tissue type defined by the appearance (e.g., intensity) within the radiological image. For example, "normal" lung tissue appears dark on CT images, which indicates negative Hounsfield units. In contrast, CV-19 tissue appears with increased opacity (e.g., brighter), and heart muscle appears more "grayish". These are based on the tissue density within the image.

The method 200 may also include generating or updating a graph-theoretic method to include the tissue signature of the lung region, as at 250. For example, the graph may be or include the scattergram 140.

The method 200 may also include generating or updating a COVID-19 classification model, as at 260. The COVID-19 classification model may be generated or updated based at least partially upon the one or more radiological images (e.g., images 102, 104, 106), the pathology results, the symptomology, the medical history, the scattergram 140, or a combination thereof. Additional details about the method 200 are provided below.

Figure 3:
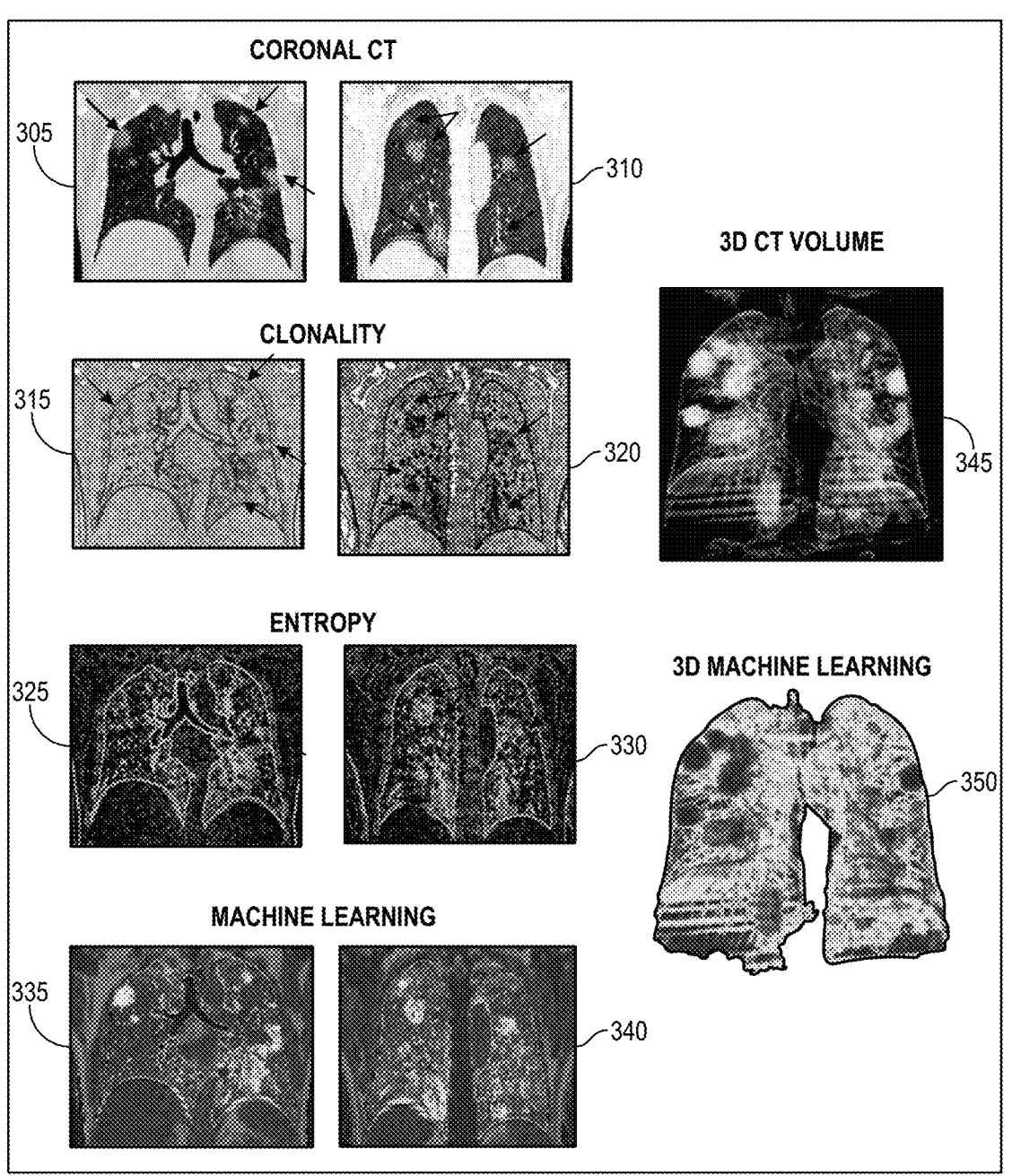
FIG. 3 illustrates a plurality of images showing radiomic features, according to an embodiment.

FIG. 3 illustrates a plurality of images showing radiomic features, according to an embodiment. More particularly, the image 305 is a coronal CT image through a first (e.g., axial) plane, and the image 310 is another coronal CT image through a second (e.g., coronal) plane. The images 305, 310 show multiple foci of ground ground-glass opacities involving one or more pulmonary lobes. As shown, the predominant distribution is in the upper and middle lung zones, where part of the opacities is located peripherally and others demonstrate a peribronchovascular distribution, as shown by the arrows.

The image 315 is a coronal clonality radiomic image through the first (e.g., axial) plane, and the image 320 is another coronal clonality radiomic image through the second (e.g., coronal) plane. The arrows in the images 315, 320 identify extensive CV-19 disease. The CV-19 features in the images 315, 320 ranged from 0.08 to 0.17. By comparison, a healthy lung ranges from 0.54 to 0.58. As used herein, the term "CV-19 feature" refers to radiomic (e.g., texture) values of each radiomic feature that represent CV-19.

The image 325 is a coronal entropy radiomic image through the first (e.g., axial) plane, and the image 330 is another coronal entropy radiomic image through the second (e.g., coronal) plane. The images 325, 330 show increased entropy in all lesions (e.g., 4.44-5.51). By comparison, a healthy lung has an entropy of about 2.56.

The image 335 is an image through the first (e.g., axial) plane after a nonlinear dimensionality reduction (NLDR) ML method has been applied to the coronal CT image 305, and the image 340 is another image through the second (e.g., coronal) plane after the NLDR ML method has been applied to the coronal CT image 310. The normal lung tissue and the areas with CV-19 lesions have been identified.

The image 345 is a 3D CT volume of the lungs, and the image 350 is the 3D CT volume of the lungs after the NLDR ML method has been applied to the image 345.

Radiomics

Radiomic methods may provide qualitative and/or quantitative textural features from radiological images (e.g., the X-ray images 202, ultrasound images 204, CT scans 206, etc.). These quantitative radiomic features may be associated with biology to provide new information about the tissue characteristics and pathology. Conventional radiomic methods extract information based on region of interest (ROI) analysis of the object of interest and the grayscale and inter-pixel patterns and many shape-based properties of the image. The use of limited ROIs results in lower visualization or interpretation of any lesion heterogeneity, tissue microenvironment, contralateral, and surrounding tissue, which diminishes the association between tissue biology of the area of interest and any local or global interpretation of disease.

Therefore, the present disclosure may produce full images and accurate detection, segmentation, and classification of lung tissue to help determine the amount of tissue damage (e.g., dur to CV-19). Thus, the present disclosure may provide improvements in localization and classification of CV-19 using ML incorporated with new radiomic features to establish new features for clinical diagnostics. Additionally, the present disclosure may allow for full image interpretation of the CV-19 lesions and surrounding lung tissue for improved radiological characterization. This information may be used for pre-therapeutic characterization by establishing baseline pulmonary status. This information may also be used to identify any potential prognostic features that may be useful in determining risk stratification. Thus, the present disclosure may determine prognostic information regarding the CV-19 burden in patients by elucidating the lung tissue in macro- and micro-environments to a degree that is currently not available with conventional methods.

Covid Radiomic Feature Mapping

A radiomic feature mapping (RFM) framework may transform each CT image 106 into a multidimensional COVID-19 radiomic feature space (CV-19 RFS), defined as CV-19 RFS={CV19RFM$_1$, CV19RFM$_2$, . . . , CV19RFM$_N$}∈R$^D$, where CV-19 RFM$_i$ represents the i$^{th}$ CV-19 radiomic feature map, D represents the number of voxels in the CT image 106, and N represents the number of CV-19 RFMs generated. The CV-19 RFM framework algorithm that transforms radiological data into the CV-19 RFS is defined below.

First, a set S of N radiomic filters from different radiomic features may be generated. The size of the neighborhood scaling parameter W may be determined by the user depending on the spatial resolution of the input CT image 106 for the radiomic feature.

Second, the quantization of the CT image 106 intensities to G levels for radiomic first and second order statistics may lead to the CT image intensities being quantized. The value of (may be determined by the user based on the range of intensities as well as the number of bits required to represent voxel intensity in the input CT image 106.

In the final step, the CT image 106 is convolved with each of the N radiomic filters in the set S to produce N radiomic feature maps. As a result, every voxel in the original CT image 106 may have a corresponding radiomic feature value in each CV-19 RFM.

The mean of the radiomic values may be calculated from different regions of interest (ROI) defined by the ML method described above for each CV-19 lesion and lung tissue. These radiomic values may then be used in each CV-19 RFM as features for classification and further analysis. Consequently, every CV-19 RFM feature from the patient corresponds to the average value taken from sliding the same sized image window (W×W) across the whole ROI ensuring there is no mathematical dependence between the computed CV-19 RFM features and size of the ROI. The radiomic features can be subdivided into five categories: First Order Statistics (FOS, 15 single features), Gray Level Co-occurrence Matrix (GLCM, 18 single features), Gray Level Run Length Matrix (GLRLM, 11 single features), Neighborhood Gray Tone Difference Matrix (NGTDM, 5 single features), fractal dimension features (2 single features) and convexity for a total of 56 radiomic features. The input parameters may be empirically determined to be G-64 and W=5.

Clonality

Clonality is a first order radiomic feature. Clonality is defined as a population of a certain type of cells within a tissue sample. Clonality may be extended for radiomic feature analysis to look at the density of certain tissue features within an image. For example, given a population of cancer cells from an individual single-cell may induce tumor heterogeneity in tissue with certain tissue signatures, and this clonality feature may map any changes in the tissue. Mathematically, clonality is defined as $$1 - \frac{-\sum p_i \log_2(p_i)}{\log_2(n)}$$

where p$_i$ is the proportion of the ith intensity feature in the image with n voxels.

Machine Learning (ML)

The ML used herein may be based on nonlinear dimension reduction (NLDR) methods that deal with nonlinearity in imaging datasets. The NLDR methods may be unsupervised ML methods that do not rely on the linearity assumption, and as a result, more complex embeddings of the data in the high-dimensional space can be identified. Isomap is an NLDR method based on geodesic distances to obtain a high-fidelity, low-dimensional representation of data. A geodesic distance is defined as one or more distances measured along the surface of the manifold. As used herein, a "manifold" refers to a topological space that is locally Euclidean near each point. The geodesic distance may be calculated and arranged in a pairwise distance matrix. The NLDR method may map some dataset X with high dimensionality D into a new dataset Y with lower dimensionality d<D), while retaining the geometry of the original data as much as possible. The geometry of the manifold and the intrinsic dimensionality d of the dataset X may not be known. Intrinsic dimensionality is defined as the minimum number of parameters needed to account for the observed properties of the data. The resulting Isomap image may provide the regions of interest (ROI) of normal and CV-19 lesions defined by the ML method described above. The ROIs may be verified by a radiologist and saved for each tissue type for radiomic analysis.

Figure 4:
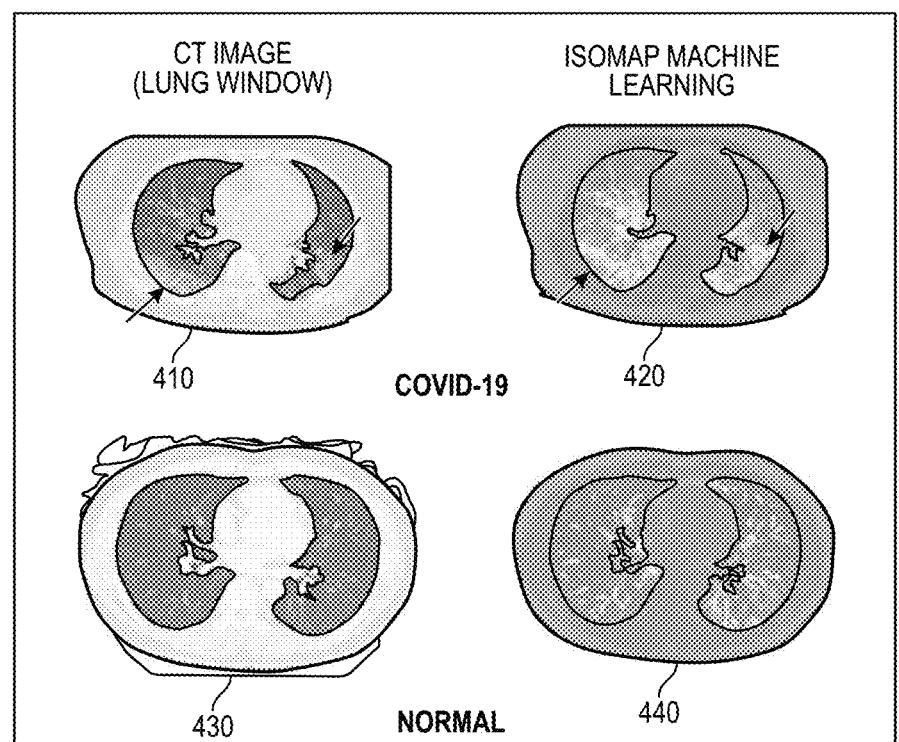
FIG. 4 illustrates a nonlinear dimensionality reduction (NLDR) machine learning (ML) method being applied to CT images, according to an embodiment.

FIG. 4 illustrates the NLDR ML method being applied to CT images, according to an embodiment. More particularly, FIG. 4 demonstrates the NLDR ML method applied to a representative subject with CV-19 (top row) and a healthy subject (bottom row), and the resulting segmentation of different lung and lesion tissue types. The image 410 is an axial CT scan at the heart level demonstrating multiple bilateral ground-glass opacities with fine intralobular septal thickening, as shown by the arrows. The image 420 is the image 410 after the NLDR ML method has been applied thereto. The image 420 more clearly demonstrates the heterogeneity of the lesion in the image 410, as shown by the arrows. The image 430 is another axial CT scan at the heart level (of a different patient). The image 440 is the image 430 after the NLDR ML method has been applied thereto.

Framework Within the IC-RADS System

Figure 5:
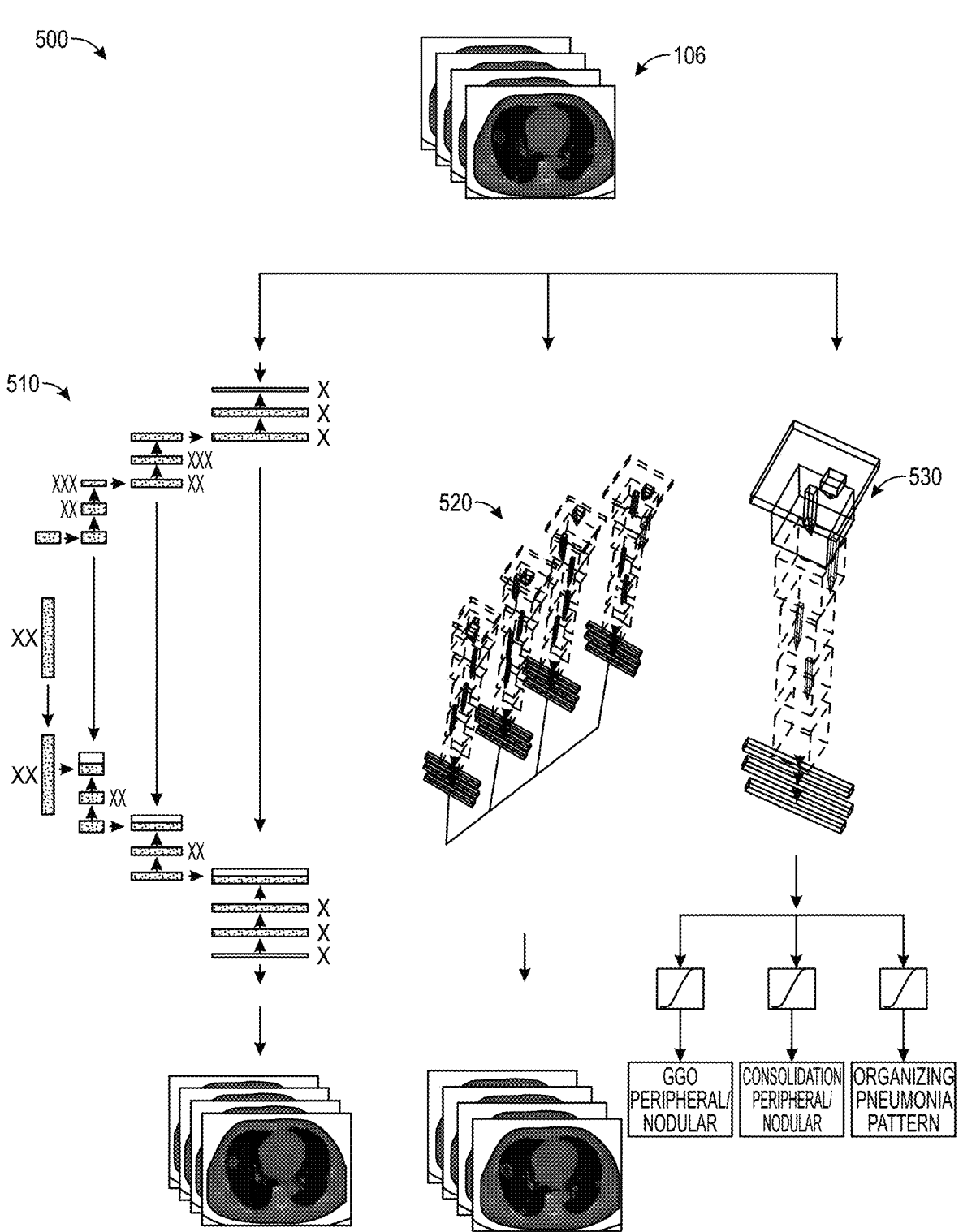
FIG. 5 illustrates a schematic view of a framework within an intelligent CV-19 radiological assessment and diagnostics system (IC-RADS) system, according to an embodiment.

A framework within the IC-RADS system may evaluate the complete radiological study, or in this example, the CT volume. Then, the framework may output a report identifying the findings. FIG. 5 illustrates a schematic view of the framework 500 within the IC-RADS system, according to an embodiment. The framework 500 may include one or more modules (three are shown: 510, 520, 530). The first module 510 may be or include a lung boundary segmentation module. The second module 520 may be or include a lung abnormality segmentation module. The third module 530 may be or include a characterization module within the IC-RADS system. The modules 510, 520, 530 may be run in series and/or parallel.

Lung Boundary Segmentation (510)

Figure 6A:
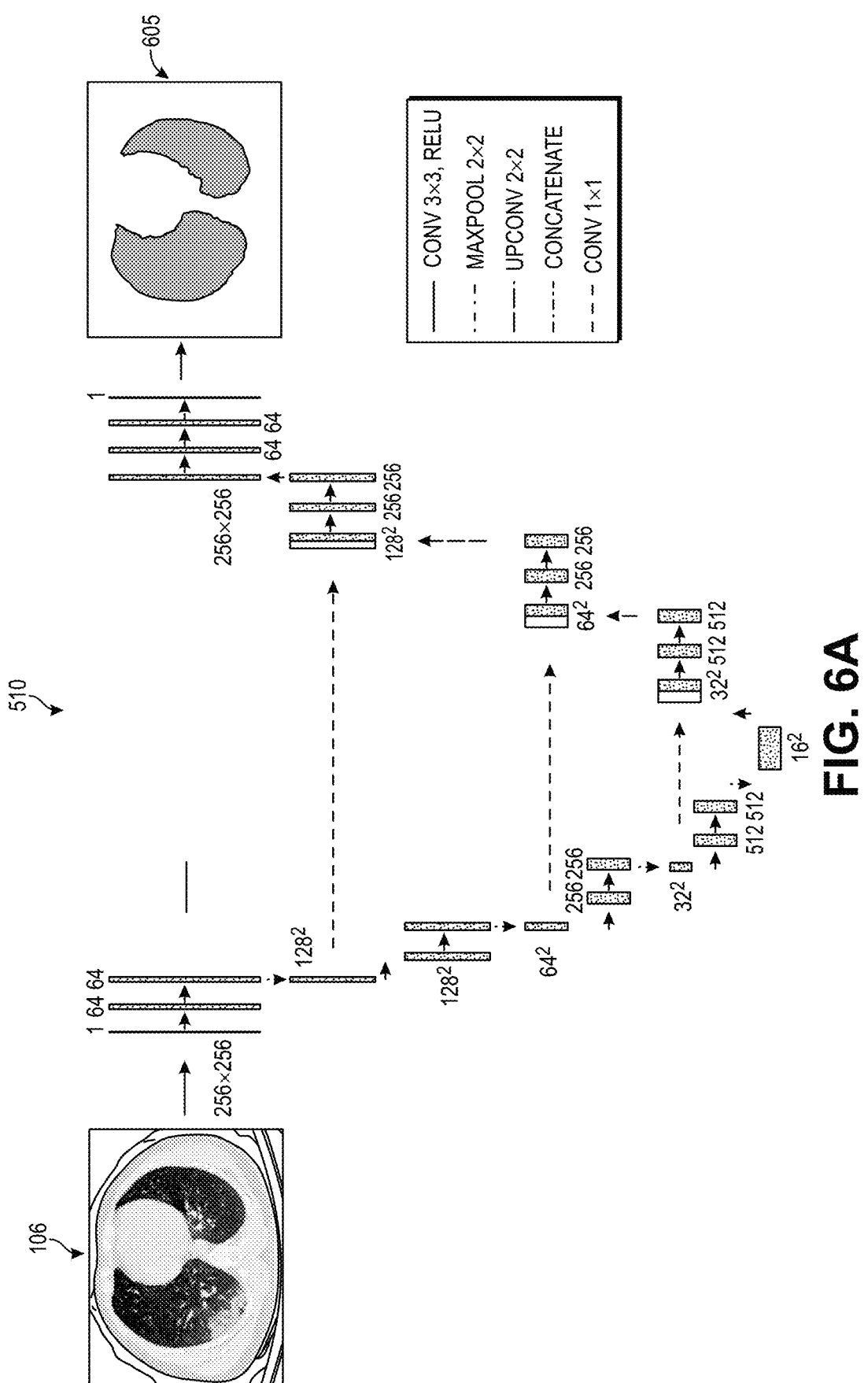
FIG. 6A illustrates a schematic view of a modified U-net architecture for total lung tissue segmentation, according to an embodiment.
Figure 6B:
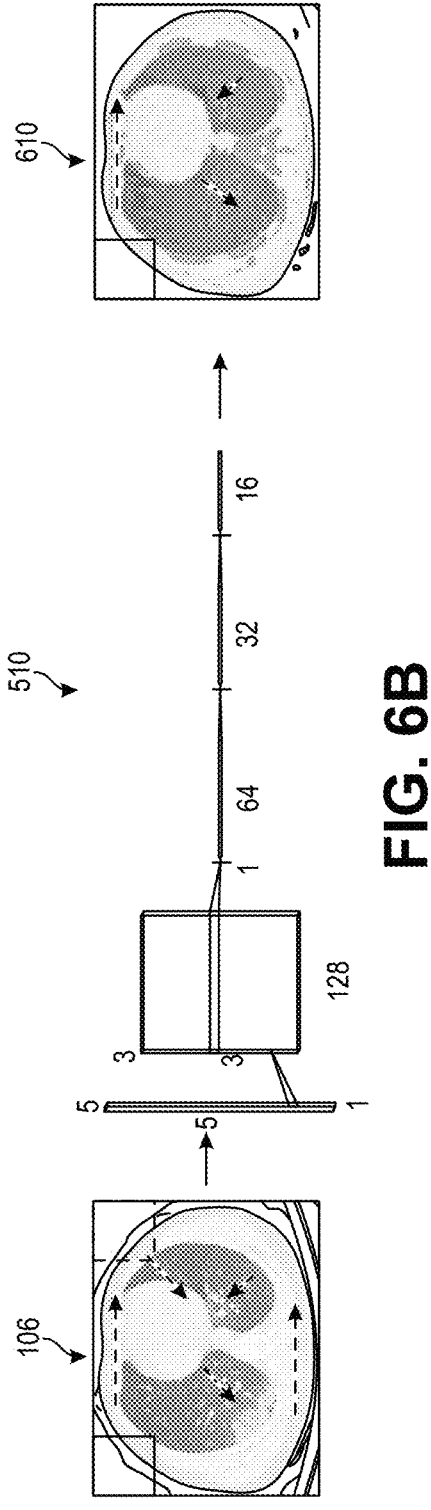
FIG. 6B illustrates a schematic view of a tissue signature patch-based convolutional neural network (CNN) used for segmentation of different healthy and abnormal tissue present in a CT image, according to an embodiment.

FIG. 6A illustrates a schematic view of a modified U-net architecture for total lung tissue segmentation, and FIG. 6B illustrates a schematic view of the tissue signature patch-based convolutional neural network (CNN) used for segmentation of different healthy and abnormal tissue present in the CT image 106, according to an embodiment. A modified semantic segmentation deep network model 510 may be based on the U-Net architecture to automatically segment the lung regions from the lung CT image 106 generated by the CT triaging module. The input to the model may be or include the lung CT image 106, and the outputs may be or include masks 605 identifying the lung areas and volumes from each of the slices found in the CT image(s) 106. The patch in FIG. 6B is the box 610. The patch 610 may be obtained by a sliding window of a predetermined size (e.g., 5×5) run across the complete image. A tissue segmentation model 510 may be based on the patch based convolutional neural network architecture to automatically segment different tissue regions (e.g., CV-19, muscle, fat, bone, etc.).

Lung Abnormality Segmentation (520)

Figure 6C:
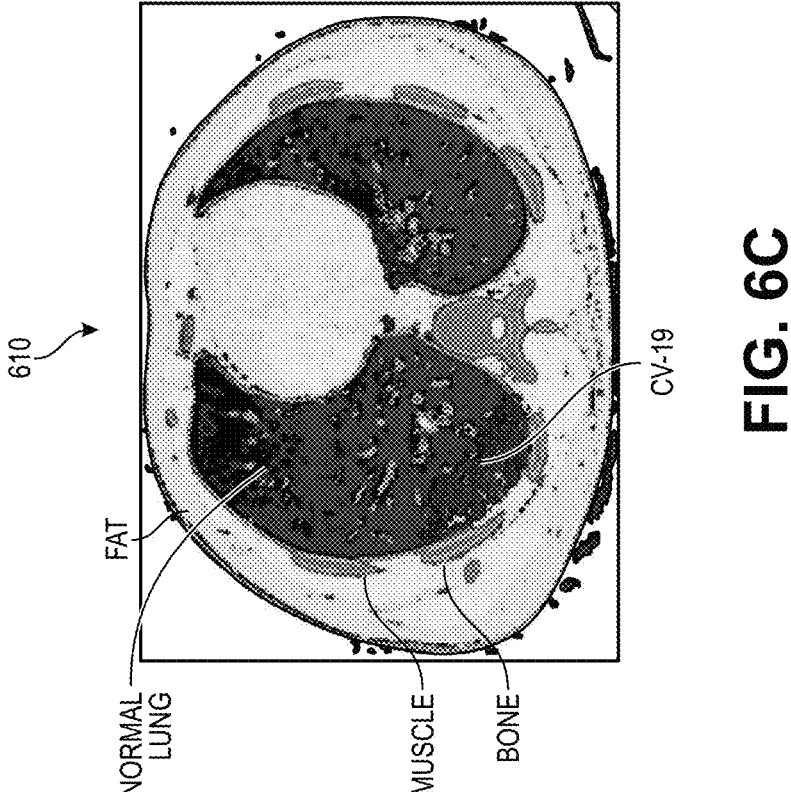
FIG. 6C is an enlarged version of the patch in FIG. 6B, according to an embodiment.
Figure 7:
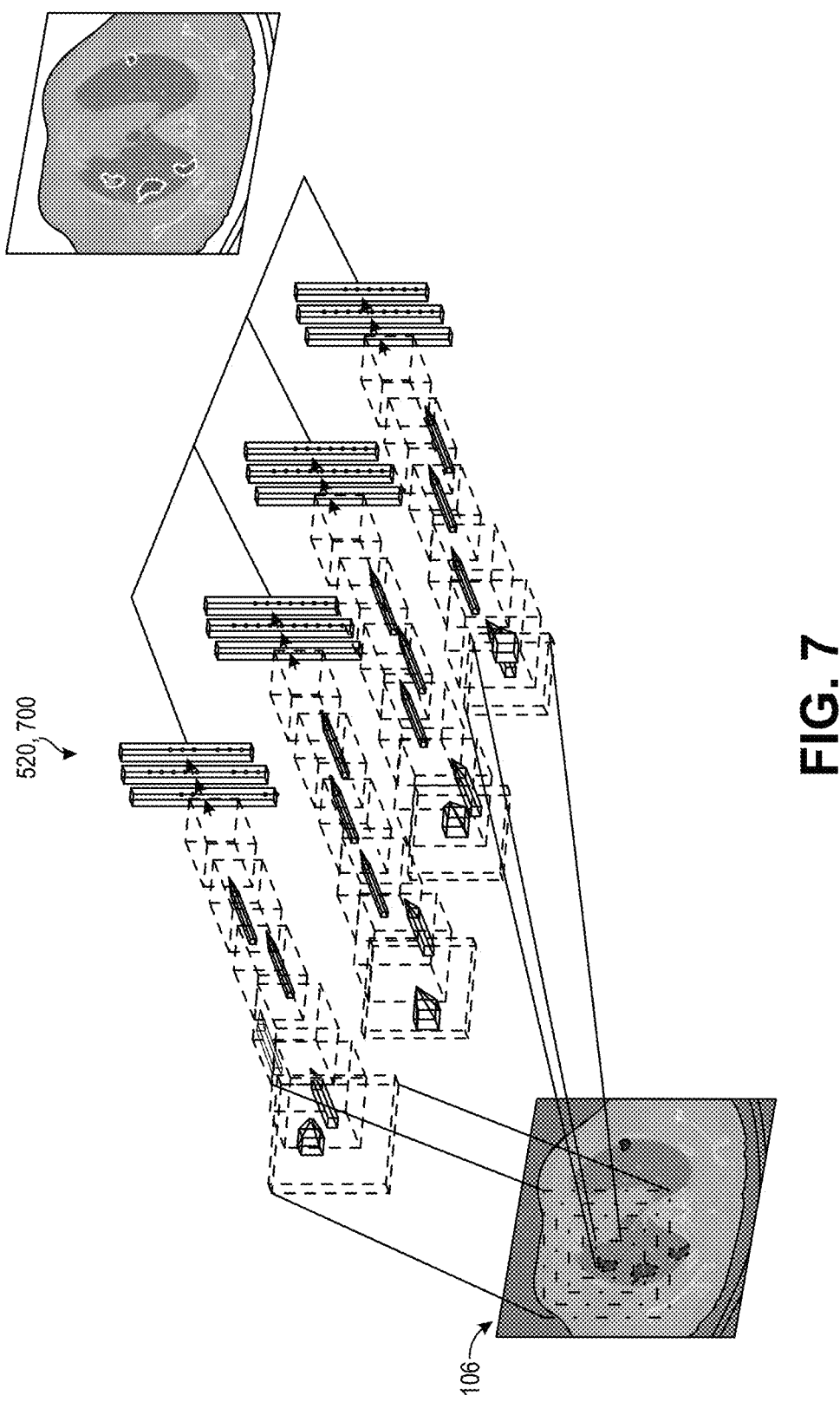
FIG. 7 illustrates a schematic view of a MTS-CNN network architecture for segmentation of CV-19, according to an embodiment.

A multiscale texture signature convolutional neural network (MTS-CNN) may be used to segment potential CV-19 regions from the lung CT image 106 generated by the CT triaging module. The input to the MTS-CNN model may be or include the lung CT image 106, and the output may correspond to the mask highlighting the CV-19 defined areas and the lung volumes defined from the CT image 106. FIG. 7 illustrates a schematic view of the MTS-CNN network architecture 700 for segmentation of CV-19, according to an embodiment. More particularly, the architecture 700 includes a deep multiscale texture signature CNN for segmentation of CV-19 lesion tissue from lungs, in addition to the heart, bone, muscle, and fat regions in CT slices, as shown in FIG. 6C, which is an enlarged version of the patch 610 on the right side of FIG. 6B.

Lung Abnormality Characterization (530)

The CV-19 characterization module may characterize the texture(s) of the CV-19 region(s) segmented by the CT segmentation and visualization module for quantifying the extent and "tissue signature" of CV-19 with a classification of ground glass opacity (GGO), crazy paving pattern, consolidation, or a combination thereof.

Lung Abnormality Characterization

Figure 8:
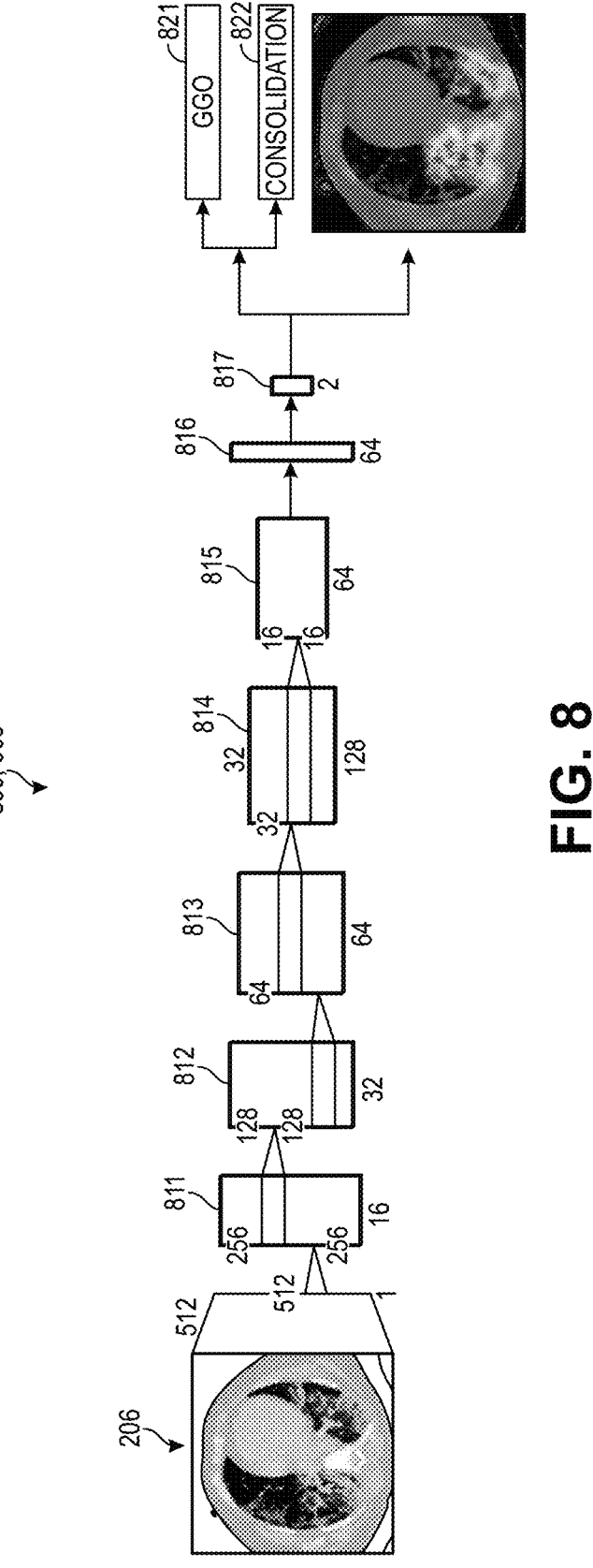
FIG. 8 illustrates a schematic view of a MTRC network model, according to an embodiment.

A multitask deep learning regression or classification (MTRC) model may be based on the tissue signature patch based CCN network for characterization of abnormalities present in the CT images 206. FIG. 8 illustrates a schematic view of the MTRC network model 800, according to an embodiment. More particularly, FIG. 8 shows the MTRC network model 800 for characterization of GGO, crazy paving pattern, and/or consolidation lung abnormalities present within the CT image 106. The model 800 may include one or more (e.g., five) convolutional layers 811-815 with 16, 32, 64, 128, and 64 layers, respectively, followed by a global average pooling layer 816, and a sigmoid layer 817. The final output classifications 821, 822 may characterize the presence or absence of an abnormality pattern detected within the CT image 106. The output 821 corresponds to the presence, and the output 822 corresponds to the absence of the underlying pattern within the lung. Below the outputs 821, 822, the class activation map is displayed as an overlay on the input CT image 106.

The multitask learning architecture may involve or use a central core architecture with the final layer including multiple output neurons, each producing a prediction of a specific task (e.g., ground glass opacity, crazy paving pattern, or consolidation). The MTRC architecture may use the inherent information sharing between the convolutional layers for each of these tasks while also ensuring mutually independent output of each task. In an example, the MTRC architecture may be trained with two initial outputs: GGO and consolidation. The output layer may use a sigmoid activation function, as opposed to the softmax activation function, because a CT lung image may be characterized by more than one lung abnormality present in the slice. For example, a lung slice may have consolidation, ground glass opacities, neither, or both. The lung slice may also or instead have other features such as fine reticulations or intralobular septal thickening.

Lung Volume Ratio

The extent of CV-19 lesions in patients may be quantified by computing the ratio between the segmented CV-19 regions and segmented lung volume by the equation below:

$$\text{Covid-19 Ratio value} = \frac{\text{COVID-19 volume}}{\text{The total lung volume}}$$

The total volume of lung present may differ between patients; however, the ratio between the abnormal and healthy lung tissue may normalize these differences and produce an unbiased metric for quantification of the extent of abnormality present in the lung tissue. The ratio may quantify the fraction of lung affected by CV-19 that is irrespective of the diversity in the lung volumes across different patients. Moreover, this metric may be used for prognostication by clinicians.

IC-RADS Contribution Scattergram (CCS)

Figure 9:
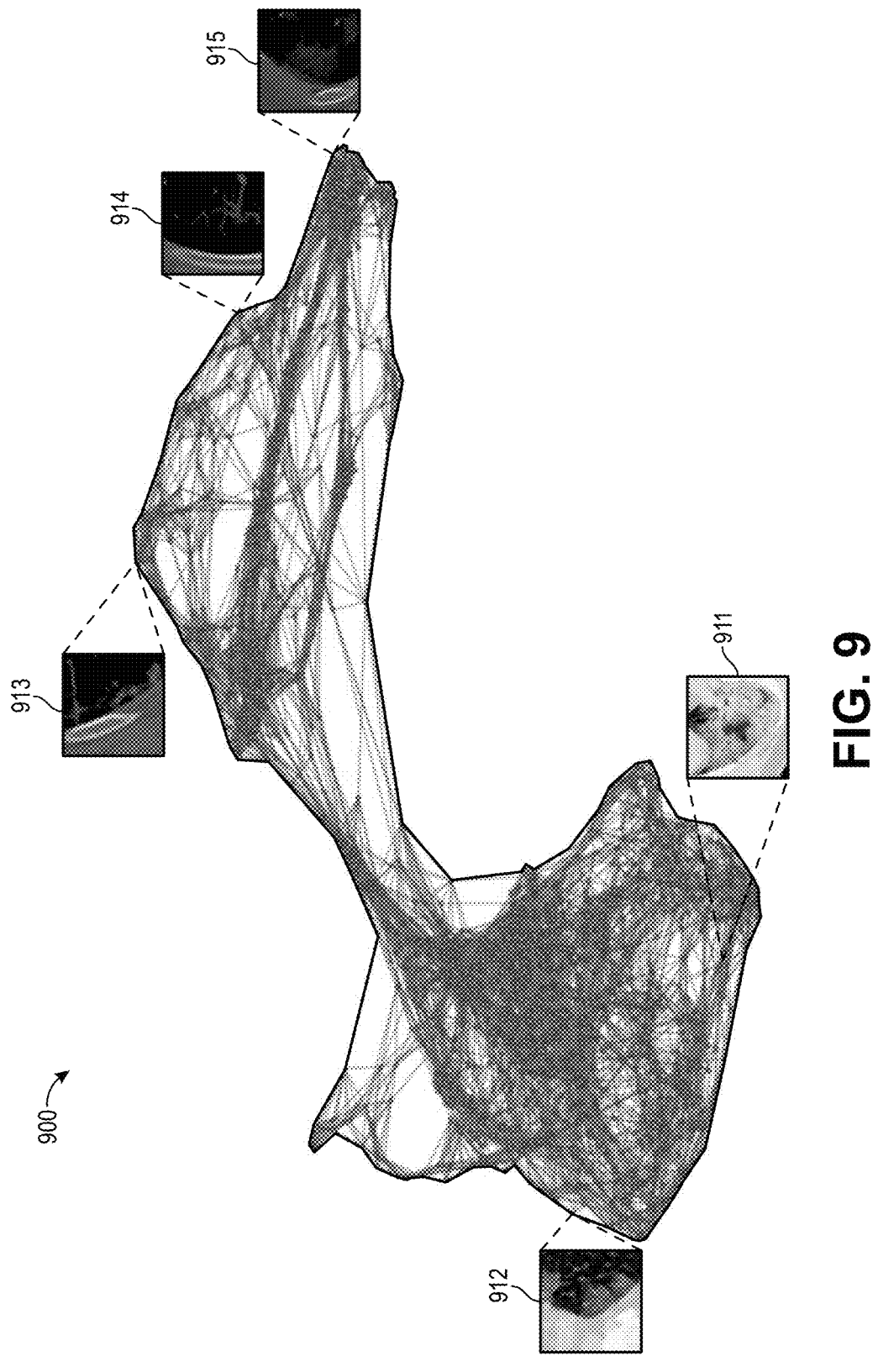
FIG. 9 illustrates a schematic view of a CV-19 contribution scattergram (CCS), according to an embodiment.

A manifold learning-based tissue signature model for CV-19 may be used to define tissue signatures based on the intrinsic appearance of CV-19 on the CT image 106. The tissue signatures may be further transformed into a risk scale using the manifold learning model to cluster similar CV-19 signatures and evaluate the risk of each tissue signature class. FIG. 9 illustrates a schematic view of a CV-19 contribution scattergram (CCS) 900, according to an embodiment. The CCS 900 may be similar to the CCS 140 in FIG. 1. The CCS 900 shows the complex interaction map between the IC-RADS radiomics, segmentation, and classification. The CCS 900 characterizes the textural tissue signatures of CV-19 across different patients with different degrees of CV-19. For example, signatures for five different patients are shown: 911-915.

Results

Figure 10:
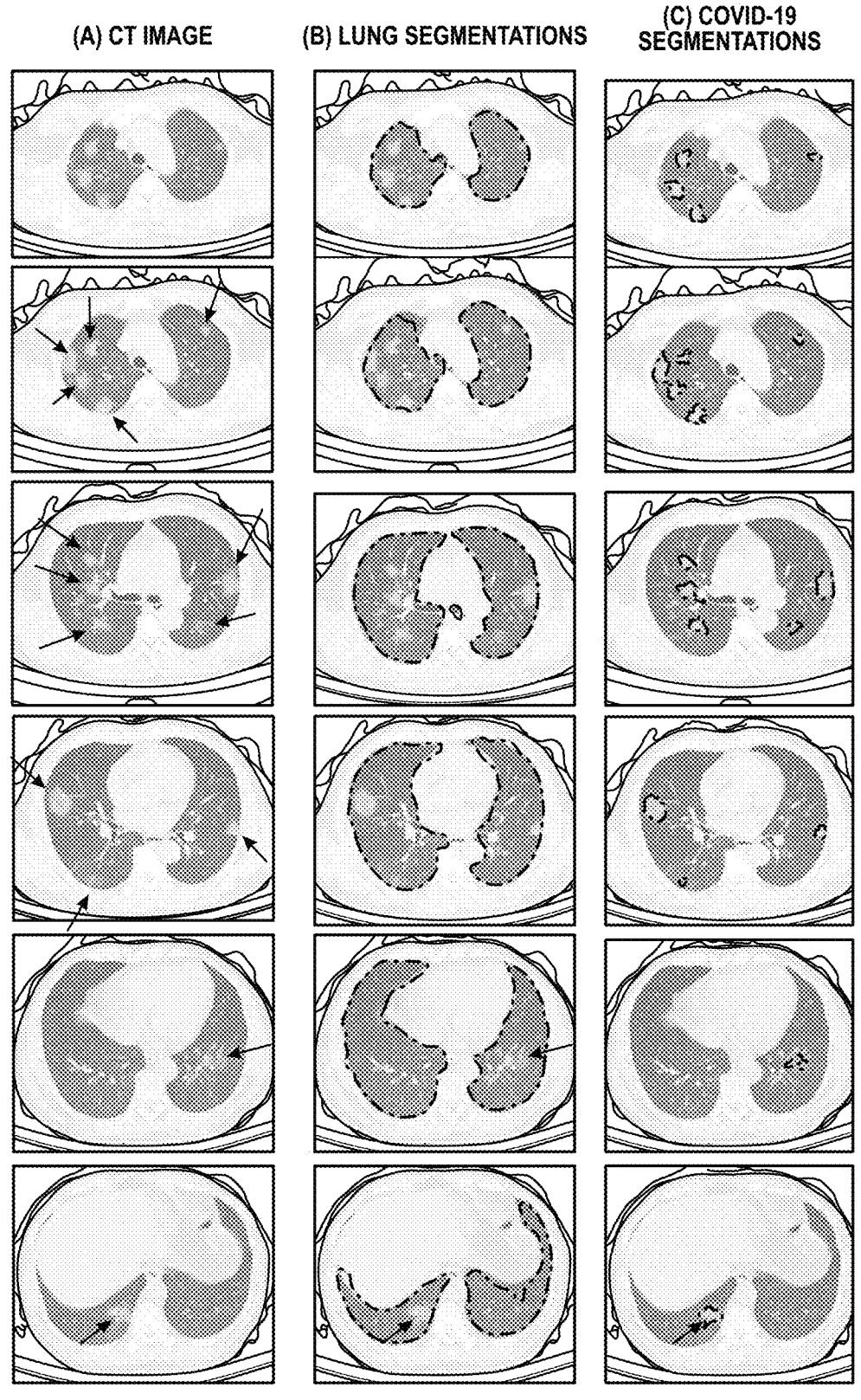
FIG. 10 illustrates lung boundary and abnormality segmentations of IC-RADS across different slices in patients, according to an embodiment.

FIGS. 10 illustrates the lung boundary and abnormality segmentations of IC-RADS across different slices in patients, according to an embodiment. The left column of FIG. 10 shows axial CT lung volume and CV-19 abnormality segmentation across multiple slices from a patient with CV-19 characteristics of nodular and peripheral ground glass opacities (as shown by the arrows). The middle column of FIG. 10 shows the lung boundary on each slide, outlined and segmented. The right column of FIG. 10 shows CV-19 segmentations (e.g., ground glass opacity segmentations). The CT images are shown using lung windowing.

Figure 11:
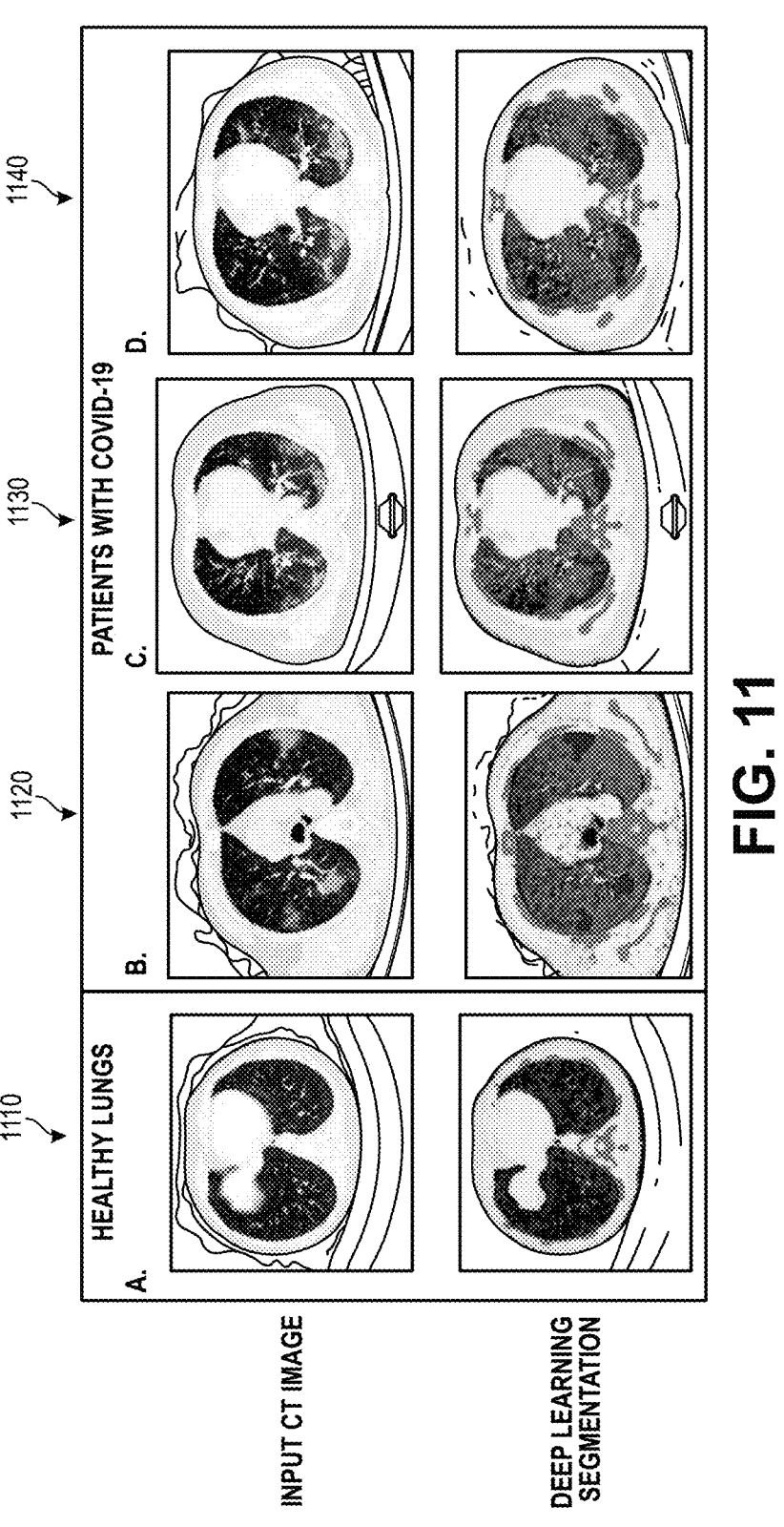
FIG. 11 illustrates a demonstration of segmentation maps obtained using the IC-RADS framework on four different patients, according to an embodiment.

FIG. 11 illustrates a demonstration of segmentation maps obtained using the IC-RADS framework on four different patients, according to an embodiment. The top row represents the input CT image, and the bottom row represents the deep learning segmentation of the input CT image. The column 1110 corresponds to a healthy lung, and the columns 1120, 1130, 1140 correspond to patients with CV-19. The lung abnormality ratios are 0.64% for column 1110, 8.26% for column 1120, 10.12% for column 1130, and 17.61% for column 1140.

FIG. 12 illustrates a demonstration of the IC-RADS output from using the CT images, according to an embodiment. The top row 1210 includes CT images at the heart level with multiple GGO lesions. The second row 1220 shows deep learning segmentation and ROI generation for the different radiological classifications of CV-19. The third row 1230 identifies the regions of CV-19 generated from the COVID: AI modules. The fourth row 1240 includes examples from the CovRAD entropy images generated from the system. The fifth row 1250 includes an example of the clonality images generated by the system showing the differences between normal and CV-19 tissue.

Figure 13:
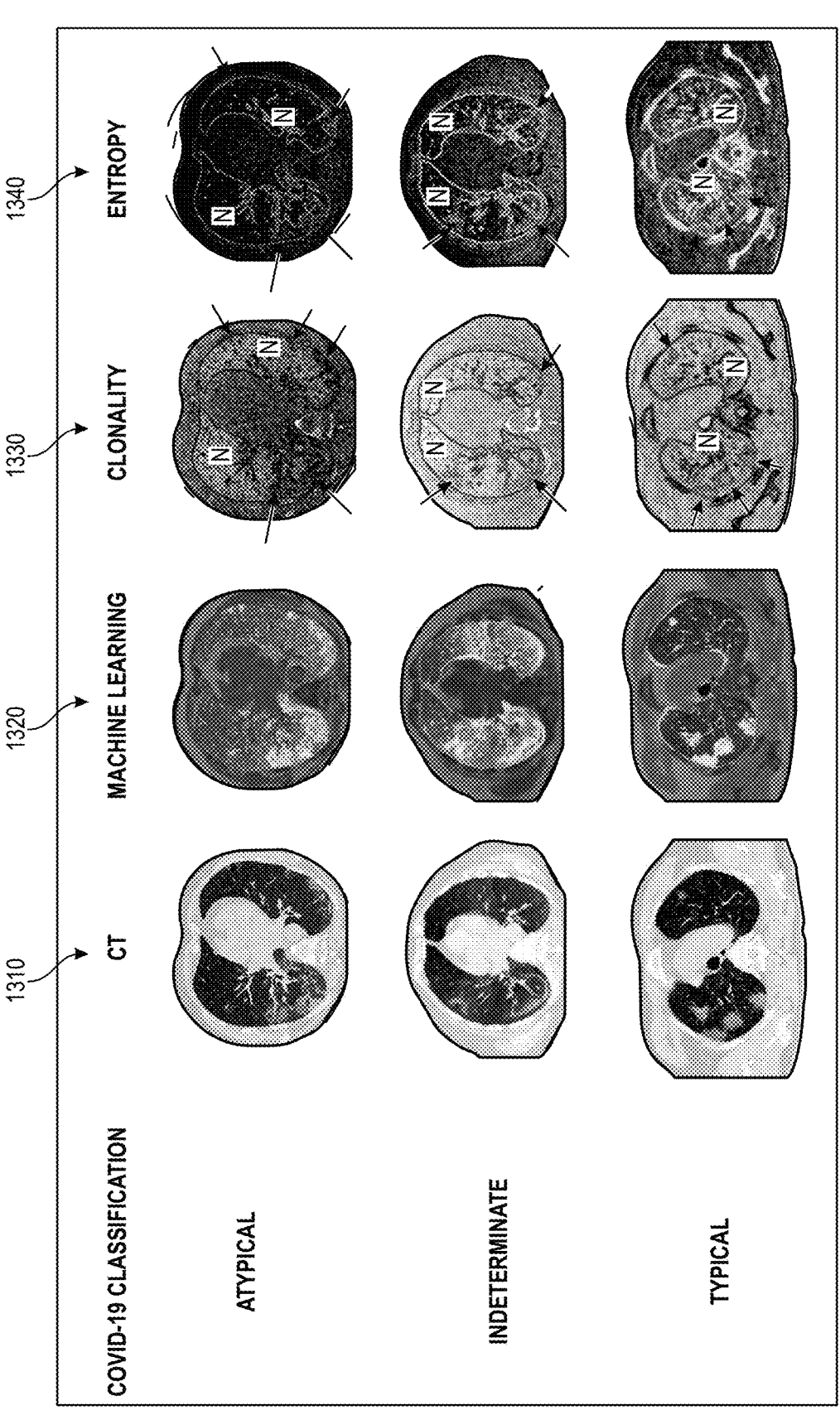
FIG. 13 illustrates an example of different radiological classifications of CV-19 and corresponding axial CT, machine learning, and clonality and entropy images, according to an embodiment.

FIG. 13 illustrates a demonstration of the different radiological classifications of CV-19 and corresponding axial CT, machine learning, and CovRad clonality and entropy images, according to an embodiment. The top row represents the atypical presentation of CV-19 in a 45-year-old man with dependent atelectasis and an interstitial pulmonary edema pattern. The middle row represents an indeterminate presentation of CV-19 in a 55-year-old man with peribronchovascular and peripheral ground glass opacities. The bottom row represents a presentation of CV-19 in a 47-year-old man with multiple ground-glass opacities involving with distributions in all pulmonary lobes with predominant distribution in the upper and middle lungs. The left column 1310 represents the CT images. The column 1320 represents the ML images. The column 1330 represents the clonality images. The right column 1340 represents the entropy images. IC-RADS can be applied in all anatomical planes of radiological scanning.

Discussion

Thus, IC-RADS may be based on a coupling of radiomics with ML and deep learning methods to provide for new quantification, visualization, and evaluation of CT images of patients with CV-19 disease. New IC-RADS features from the lungs of the CV-19 patients may be compared to healthy lung tissue. The CV-19 lung lesions may be different than healthy lung features. For example, CV-19 lesions in the lungs with GGO with consolidation or non-round GGO may have a substantial higher entropy and lower clonality compared to healthy lungs, as well as the other radiomic metrics. The healthy lung tissue in patients with CV-19 disease may not be different in the IC-RADS metrics when compared to lung tissue in healthy subjects. The present disclosure may be used to study and define quantitative radiomic metrics of CV-19 lesions in patients using CT images. However, these methods may be expanded to US, MRI, or other radiological methods. IC-RADS presents a whole-image visualization of different quantitative metrics, which may add to further interpretation and classification CV-19 patients and provide a monitoring tool for treatment follow up.

The IC-RADS framework may provide a new fast implementation of machine and deep learning systems for automated detection, diagnosis, and characterization of CV-19 from radiological imaging. The IC-RADS framework is a new fast implementation of a radiomics system for automated detection, diagnosis, and characterization of COVID-19 from radiological imaging. The IC-RADS framework generates a radiological report based on the standardized reporting guidelines by "reading" the radiological imaging volume. The IC-RADS framework characterizes the lung abnormality based on the standardized set of features defined by the current standard (e.g., ground glass opacity, crazy paving pattern, consolidation, etc.) and creates radiomic images. The IC-RADS framework characterizes the extent of lung abnormality by automatically computing lung ratios defined by the COVID index. The IC-RADS framework identifies images and highlights these slices in the radiological dataset. The IC-RADS framework may enable physicians to navigate to directly navigate to key slices and different body regions (e.g., heart, liver, lung). The IC-RADS framework may produce a segmentation of the radiological image of the different tissue types, such as, the fatty tissue, muscle, bone, heart, normal and abnormal lung, etc. The IC-RADS framework may provide an embedded map for image modelling system to synthetically create normal and abnormal radiological images for accelerated AI development. The IC-RADS framework may provide a method to extract relevant features from diagnostics defined as blood work, smears, PCR-RT, etc. The IC-RADS framework may provide a method to extract relevant features from Electronic Health Records defined as patient visits, physical exams, symptomology, text of the diagnostics, (e.g., metabolic values, complete blood counts, heart rate, blood pressure, etc.). The IC-RADS creates a relationship that maps each type of lung abnormality to a point in an image space (2D) or 3D, thereby creating a discovery platform for identifying existing and new patterns of lung abnormalities. The IC-RADS system may determine the interrelationships and patterns between the diagnostics and imaging data, which enables accurate detection and contribution of each COVID-19 abnormality to the patient population. The IC- RADS system may not use any prior knowledge about the number and types of COVID-19 patterns present in the patient population. The IC-RADS system may perform a virtual biopsy by unsupervised pattern analysis of radiomic and radiological characterization of normal and abnormal lung tissue. The IC-RADS system may produce a heatmap on any type of ontologies (e.g., images, diagnostics, health records, or digital data). The IC-RADS may produce a complex interaction map on any type of ontologies (e.g., images, diagnostics, health records, or digital data). The IC-RADS may determine the interrelationships and patterns, which enables accurate detection and contribution of each data parameter to the dimensional space.

Figure 14:
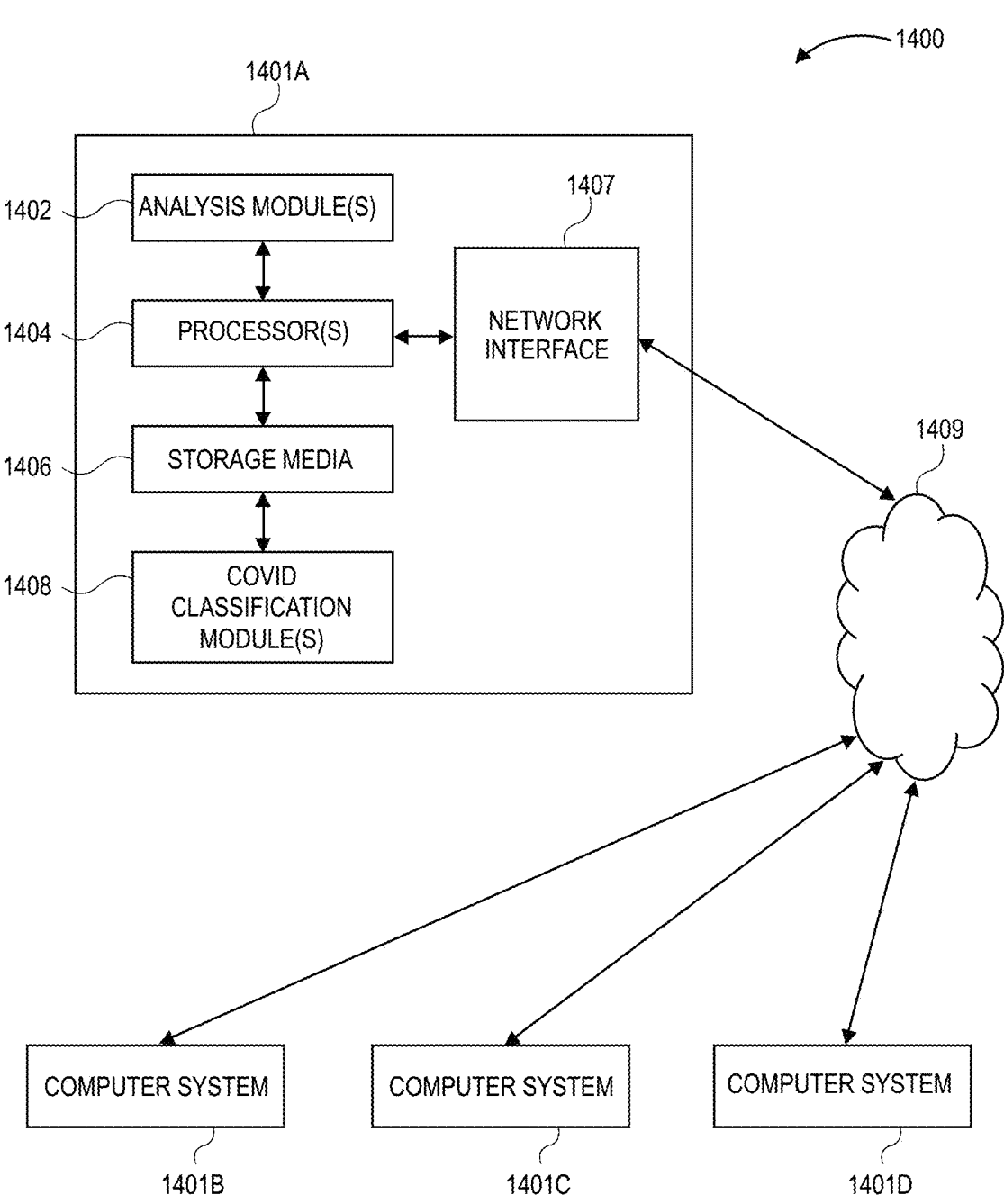
FIG. 14 illustrates a schematic view of an example of a computing system for performing at least a portion of the method(s) disclosed herein, according to an embodiment.

FIG. 14 illustrates a schematic view of an example of a computing system 1400 for performing at least a portion of the method 200, according to an embodiment. The computing system 1400 may include a computer or computer system 1401A, which may be an individual computer system 1401A or an arrangement of distributed computer systems. The computer system 1401A includes one or more analysis modules 1402 that are configured to perform various tasks according to some embodiments, such as one or more methods disclosed herein. To perform these various tasks, the analysis module 1402 executes independently, or in coordination with, one or more processors 1404, which is (or are) connected to one or more storage media 1406A. The processor(s) 1404 is (or are) also connected to a network interface 1407 to allow the computer system 1401A to communicate over a data network 1409 with one or more additional computer systems and/or computing systems, such as 1401B, 1401C, and/or 1401D (note that computer systems 1401B, 1401C and/or 1401D may or may not share the same architecture as computer system 1401A, and may be located in different physical locations, e.g., computer systems 1401A and 1401B may be located in a processing facility, while in communication with one or more computer systems such as 1401C and/or 1401D that are located in one or more data centers, and/or located in varying countries on different continents).

A processor can include a microprocessor, microcontroller, processor module or subsystem, programmable integrated circuit, programmable gate array, or another control or computing device.

The storage media 1406A can be implemented as one or more computer-readable or machine-readable storage media. Note that while in the example embodiment of FIG. 14 storage media 1406A is depicted as within computer system 1401A, in some embodiments, storage media 1406A may be distributed within and/or across multiple internal and/or external enclosures of computing system 1401A and/or additional computing systems. Storage media 1406A may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLUERAY® disks, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some embodiments, computing system 1400 contains one or more CV-19 classification module(s) 1408 which may be used to perform at least a portion of the method 200. It should be appreciated that computing system 1400 is only one example of a computing system, and that computing system 1400 may have more or fewer components than shown, may combine additional components not depicted in the example embodiment of FIG. 14, and/or computing system 1400 may have a different configuration or arrangement of the components depicted in FIG. 14. The various components shown in FIG. 14 may be implemented in hardware, software, or a combination of both hardware and software, including one or more signal processing and/or application specific integrated circuits.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A computing system for detecting and characterizing COVID-19 tissue in a lung region of a patient, the computing system comprising:

one or more processors; and a memory system comprising one or more non-transitory computer-readable media storing instructions that, when executed by at least one of the one or more processors, cause the computing system to perform operations, the operations comprising:

receiving one or more radiological images of an anatomy of a patient, pathology results for the patient, symptomology for the patient, and a medical history of the patient;

running an artificial intelligence model based at least partially upon the one or more radiological images, the pathology results, the symptomology, and the medical history, wherein running the artificial intelligence model comprises:

identifying a boundary of different tissue types in the anatomy of the patient using a semantic segmentation model;

identifying one or more regions within the boundary using a multiscale texture signature convolutional neural network (MTS-CNN) model, wherein the one or more regions comprise a lung region, a heart region, a liver region, a bone region, a muscle region, and a fat region;

characterizing textures of the one or more regions using radiomics;

identifying healthy tissue and COVID-19 tissue in the lung region;

classifying one or more segments of the COVID-19 tissue in the lung region as ground glass opacity, crazy paving pattern, consolidation, or a combination thereof based at least partially upon the one or more radiological images and the textures, wherein the one or more segments are classified using a multitask regression and classification (MTRC) model;

quantifying an extent of the COVID-19 tissue in the lung region as a ratio by comparing an amount of the COVID-19 tissue in the lung region to an amount of the healthy tissue in the lung region; and classifying the extent of the COVID-19 tissue in the lung region into one or more of a plurality of COVID-19 classes defined by radiological nomenclature;

determining a tissue signature of the lung region based at least partially upon the classification of the extent of the COVID-19 tissue in the lung region;

generating or updating a scattergram to include the tissue signature of the lung region; and generating or updating a COVID-19 classification model based at least partially upon the one or more radiological images, the pathology results, the symptomology, the medical history, and the scattergram.

2. The computing system of claim 1, wherein the radiological images comprise computed tomography (CT) images.

3. The computing system of claim 1, wherein the artificial intelligence model uses machine learning, deep learning, radiomics, and complex network analysis.

4. The computing system of claim 1, wherein characterizing the textures of the one or more regions using radiomics comprises characterizing the textures of the one or more regions using clonality.

5. The computing system of claim 1, wherein the classes comprise: typical, atypical, and indeterminate.

6. A method for detecting and characterizing COVID-19 tissue, the method comprising:

receiving one or more radiological images of an anatomy of a patient;

running an artificial intelligence model based at least partially upon the one or more radiological images, wherein running the artificial intelligence model comprises:

identifying a boundary of different tissue types in the anatomy of the patient using a semantic segmentation model;

identifying one or more regions within the boundary using a multiscale texture signature convolutional neural network (MTS-CNN) model, wherein the one or more regions comprise a lung region;

identifying healthy tissue and COVID-19 tissue in the lung region;

classifying one or more segments of the COVID-19 tissue in the lung region based at least partially upon the one or more radiological images, wherein the one or more segments are classified using a multitask regression and classification (MTRC) model;

quantifying an extent of the COVID-19 tissue in the lung region as a ratio by comparing an amount of the COVID-19 tissue in the lung region to an amount of the healthy tissue in the lung region; and classifying the extent of the COVID-19 tissue in the lung region into one or more of a plurality of COVID-19 classes;

determining a tissue signature of the lung region based at least partially upon the classification of the extent of the COVID-19 tissue in the lung region; and generating or updating a scattergram to include the tissue signature of the lung region.

7. The method of claim 6, further comprising receiving pathology results for the patient, symptomology for the patient, and a medical history of the patient, wherein the artificial intelligence model is run based at least partially upon the pathology results, the symptomology, and the medical history.

8. The method of claim 6, wherein the one or more regions further comprise a heart region, a liver region, a bone region, a muscle region, and a fat region.

9. The method of claim 6, further comprising characterizing textures of the one or more regions using radiomics.

10. The method of claim 9, wherein the one or more segments are classified as ground glass opacity, crazy paving pattern, consolidation, or a combination thereof, and wherein the one or more segments are classified based at least partially upon the textures.

11. The method of claim 6, further comprising generating or updating a COVID-19 classification model based at least partially upon the one or more radiological images and the scattergram.

12. A method, comprising:

receiving one or more radiological images of an anatomy of a patient;

identifying a boundary of different tissue types in the anatomy of the patient based at least partially upon the one or more radiological images, wherein the boundary is identified using a semantic segmentation model;

identifying one or more regions within the boundary, wherein the one or more regions comprise a lung region, wherein the one or more regions are identified using a multiscale texture signature convolutional neural network (MTS-CNN) model;, and wherein the one or more segments are classified using a multitask regression and classification (MTRC) model;

identifying healthy tissue and COVID-19 tissue in the lung region;

quantifying an extent of the COVID-19 tissue in the lung region by comparing an amount of the COVID-19 tissue in the lung region to an amount of the healthy tissue in the lung region;

and classifying the extent of the COVID-19 tissue in the lung region into one or more of a plurality of COVID-19 classes.

13. The method of claim 12, further comprising running a model based at least partially upon the one or more radiological images, wherein running the model comprises:

identifying the boundary;

identifying the one or more regions;

identifying the healthy tissue and COVID-19 tissue;

quantifying the extent of the COVID-19 tissue in the lung region; and classifying the extent of the COVID-19 tissue.

14. The method of claim 12, further comprising characterizing textures of the one or more regions using radiomics.

15. The method of claim 14, further comprising classifying one or more segments of the COVID-19 tissue in the lung region based at least partially upon the one or more radiological images.

16. The method of claim 15, wherein the one or more segments are classified based at least partially upon the textures, and wherein the one or more segments are classified as ground glass opacity, crazy paving pattern, consolidation, or a combination thereof.

17. The method of claim 12, further comprising determining a tissue signature of the lung region based at least partially upon the classification of the extent of the COVID-19 tissue in the lung region.

18. The method of claim 17, further comprising generating or updating a scattergram to include the tissue signature of the lung region.

19. The method of claim 18, further comprising generating or updating a COVID-19 classification model based at least partially upon the one or more radiological images and the scattergram.

* * * * *